United States Patent [19]
Houser et al.

[11] Patent Number: 6,063,098
[45] Date of Patent: May 16, 2000

[54] ARTICULABLE ULTRASONIC SURGICAL APPARATUS

[76] Inventors: Kevin Houser, 629 Banbury Rd., Centerville, Ohio 45459; Stephen DiMatteo, 3 Hiawatha Rd., Plymouth, Mass. 02360

[21] Appl. No.: 09/059,472

[22] Filed: Apr. 13, 1998

Related U.S. Application Data

[63] Continuation-in-part of application No. 08/770,550, Dec. 23, 1996.

[51] Int. Cl.⁷ ..................................................... A61B 17/32
[52] U.S. Cl. ........................................... 606/169; 606/170
[58] Field of Search ............................... 606/2, 169, 170, 606/171, 205, 45–52; 604/22

[56] References Cited

U.S. PATENT DOCUMENTS

| | | |
|---|---|---|
| 4,674,501 | 6/1987 | Greenberg . |
| 5,026,387 | 6/1991 | Thomas . |
| 5,156,143 | 10/1992 | Bocquet et al. ......................... 604/22 |
| 5,158,086 | 10/1992 | Brown et al. . |
| 5,322,055 | 6/1994 | Davison et al. . |
| 5,330,502 | 7/1994 | Hassler et al. . |
| 5,383,888 | 1/1995 | Zvenyatsky et al. . |
| 5,391,180 | 2/1995 | Tovey et al. . |
| 5,403,342 | 4/1995 | Tovey et al. . |
| 5,409,498 | 4/1995 | Braddock et al. . |
| 5,411,519 | 5/1995 | Tovey et al. . |
| 5,413,107 | 5/1995 | Oakley et al. . |
| 5,417,203 | 5/1995 | Tovey et al. . |
| 5,431,323 | 7/1995 | Smith et al. . |
| 5,456,401 | 10/1995 | Green et al. . |
| 5,472,439 | 12/1995 | Hurd . |
| 5,478,003 | 12/1995 | Green et al. . |
| 5,482,197 | 1/1996 | Green et al. . |
| 5,490,819 | 2/1996 | Nicholas et al. . |
| 5,501,654 | 3/1996 | Failla et al. . |
| 5,514,157 | 5/1996 | Nicholas et al. . |
| 5,562,682 | 10/1996 | Oberlin et al. . |
| 5,564,615 | 10/1996 | Bishop et al. . |
| 5,575,799 | 11/1996 | Bolanos et al. . |
| 5,607,095 | 3/1997 | Smith et al. . |
| 5,607,450 | 3/1997 | Zvenyatsky et al. . |
| 5,609,601 | 3/1997 | Kolesa et al. . |

OTHER PUBLICATIONS

*Harmonic Scalpel Operating Manual*, UltraCision, Incorporated, Rev. N3/95.

Catalog p. No. 187, Flexbar Catalog No. 196, 1996.

*Primary Examiner*—Michael Buiz
*Assistant Examiner*—William Lewis
*Attorney, Agent, or Firm*—Verne E. Kreger

[57] ABSTRACT

An ultrasonic surgical clamp coagulator apparatus is configured to effect cutting, coagulation, and clamping of tissue by cooperation of a clamping mechanism of the apparatus with an associated ultrasonic end-effector. Selective articulational positioning of the end-effector is achieved by the provision of an articulating mechanism incorporated into the clamp coagulator apparatus. The arrangement permits an elongated portion of the apparatus to be selectively articulatably positioned with respect to an apparatus housing.

28 Claims, 7 Drawing Sheets

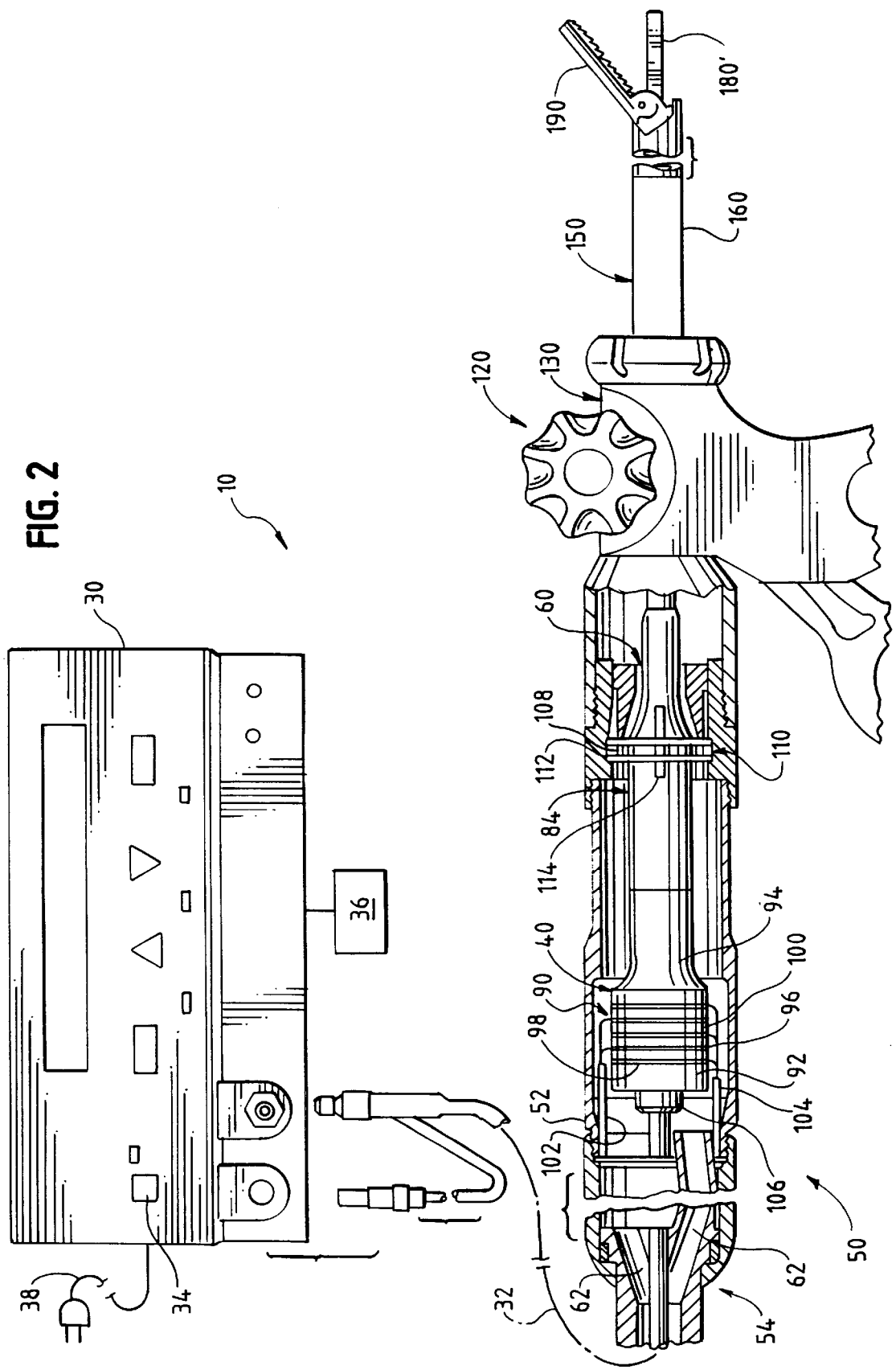

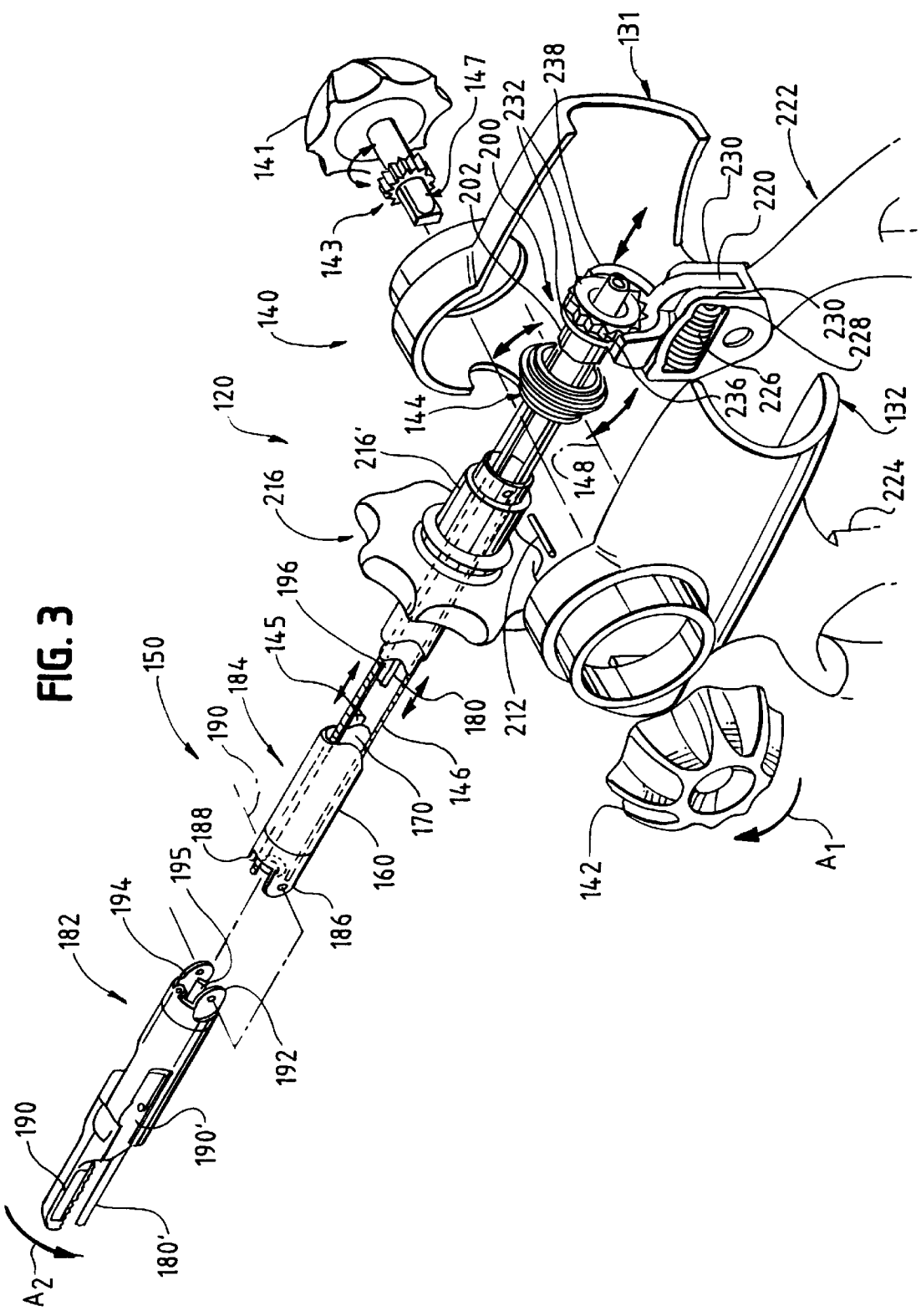

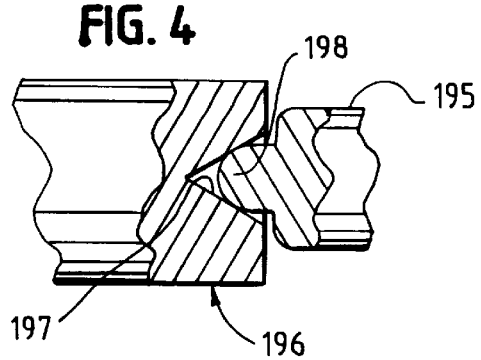
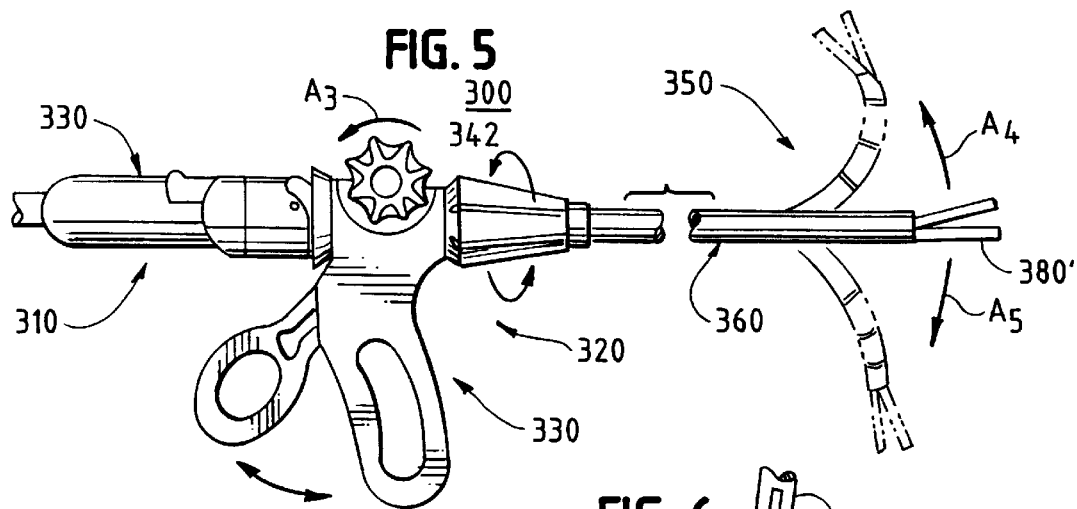
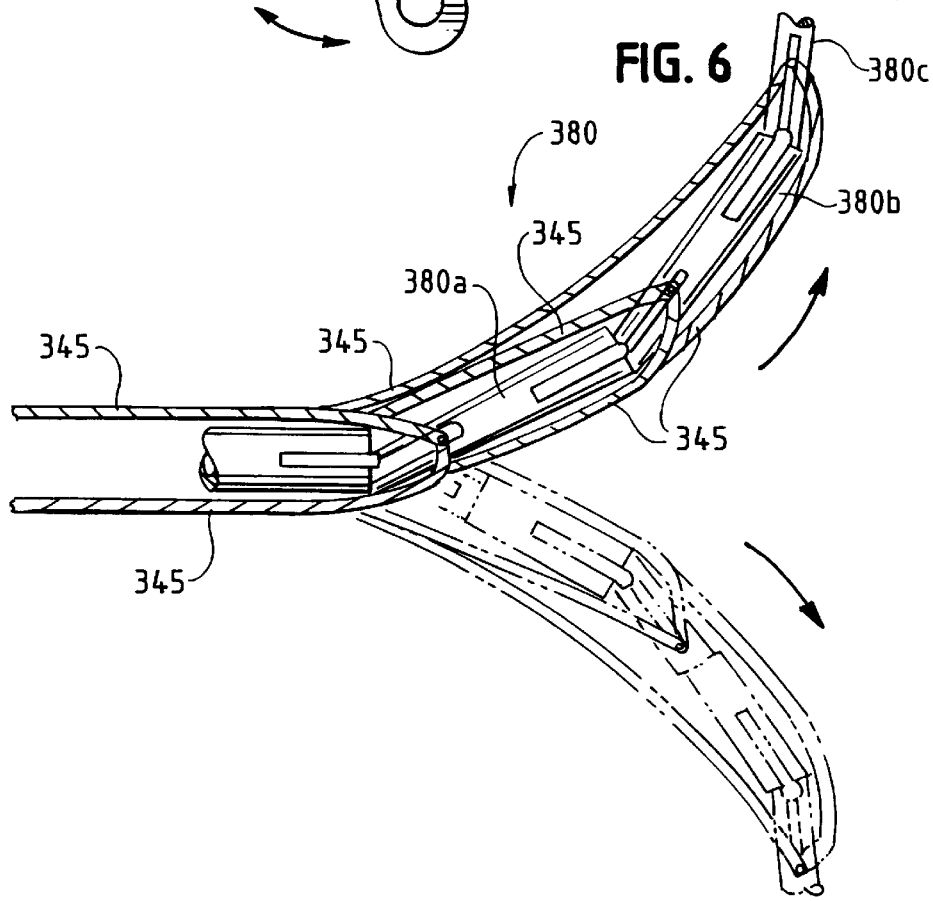

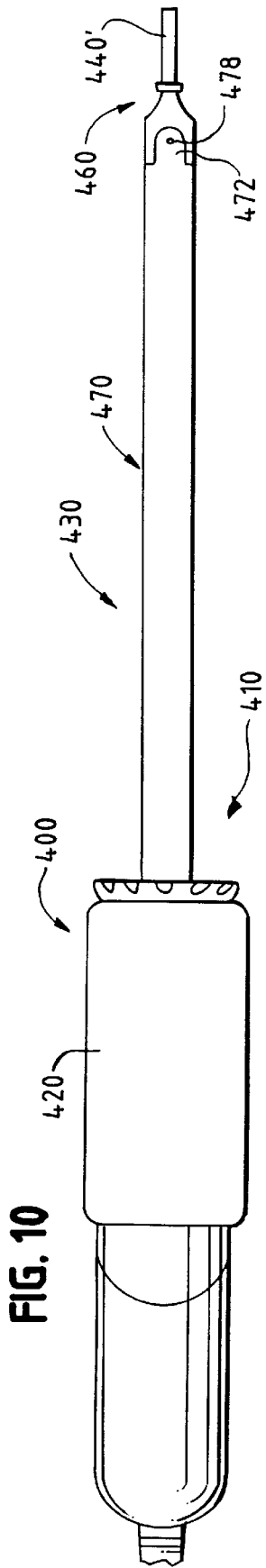
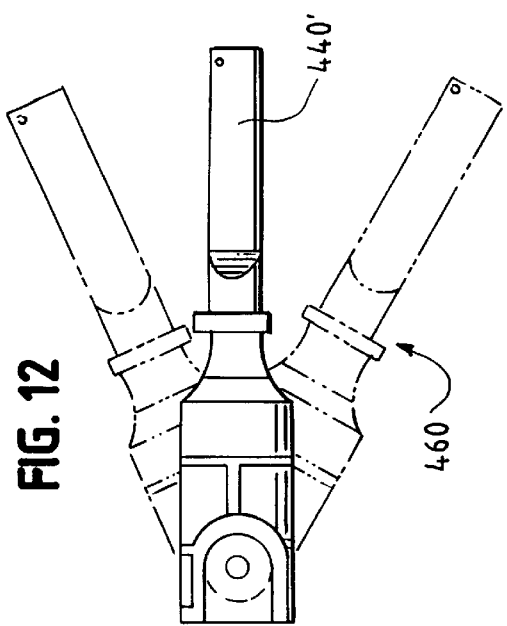
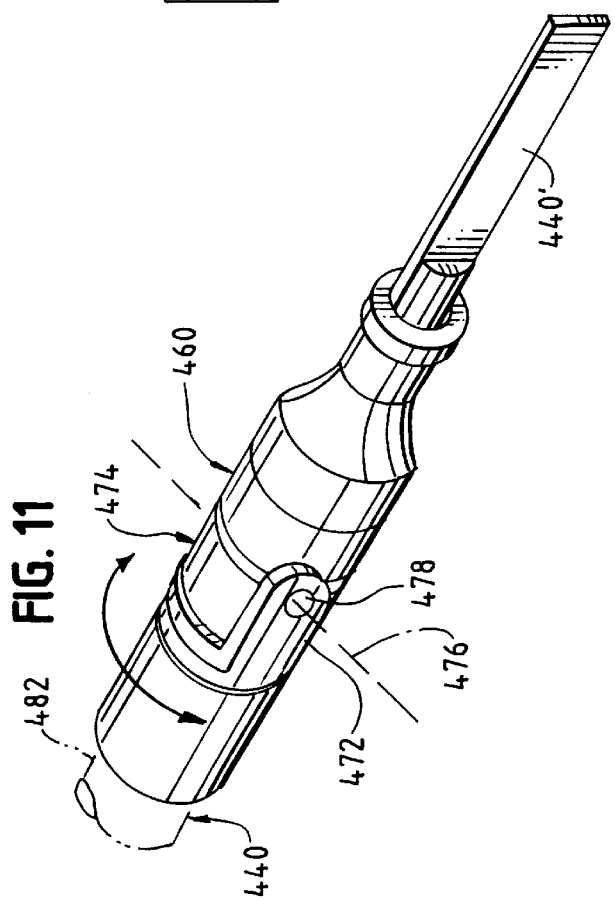
FIG. 10
FIG. 12
FIG. 11

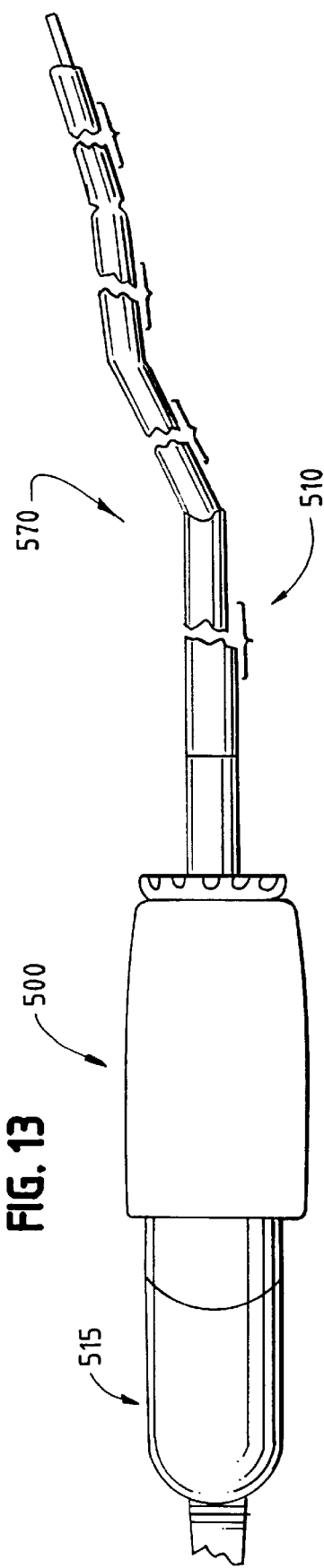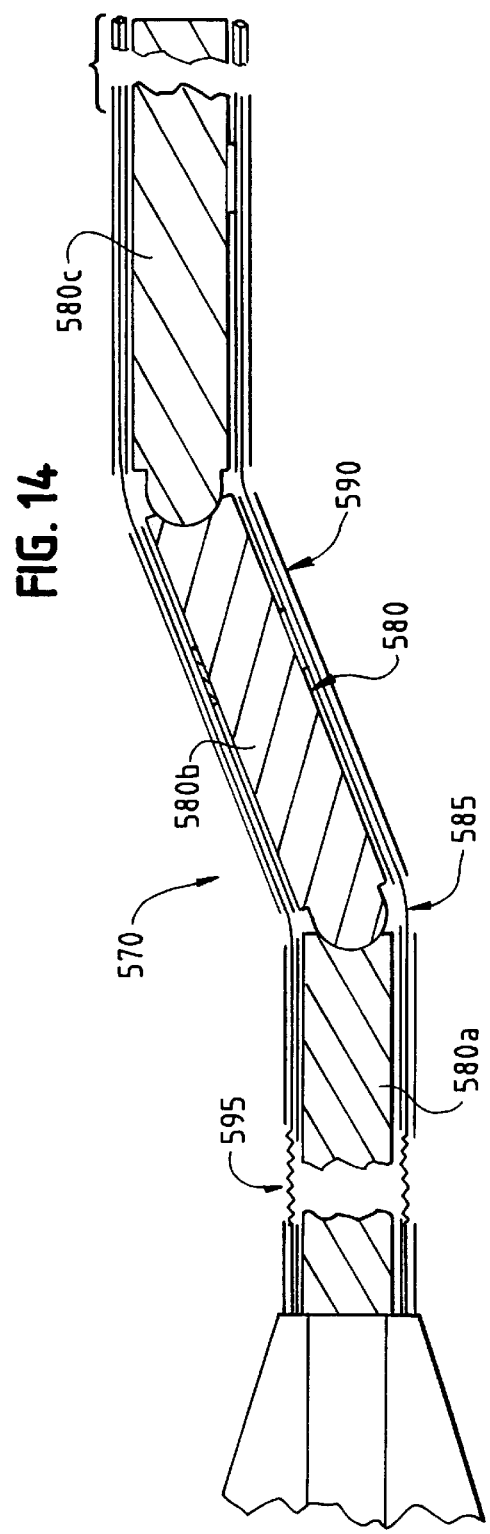

ARTICULABLE ULTRASONIC SURGICAL APPARATUS

RELATED APPLICATIONS

This is a continuation-in-part of application Ser. No. 08/770,550 filed Dec. 23, 1996, still pending.

TECHNICAL FIELD

The present invention relates generally to ultrasonic surgical apparatus, and more particularly to ultrasonic surgical apparatus for coagulation and/or cutting tissue, including an ultrasonic waveguide and/or end-effector that can be angularly and rotatably positioned.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end-effector at the distal end of the instrument, with the end-effector transmitting ultrasonic energy to tissue brought into contact therewith. Ultrasonic instruments of this nature can be configured for open surgical use, or laparoscopic or endoscopic surgical procedures.

Ultrasonic surgical instruments have been developed that include a clamp mechanism to press tissue against the end-effector of the instrument in order to couple ultrasonic energy to the tissue of a patient. Such an arrangement (sometimes referred to as an ultrasonic transector) is disclosed in U.S. Pat. No. 5,322,055, hereby incorporated by reference. Typical constructions have included a waveguide having an end-effector extending in a longitudinal direction from the handle or handpiece of the instrument. However, the angle of the end-effector and/or waveguide usually cannot be selectively adjusted in relation to the handle. Therefore, a surgeon using the surgical apparatus may not be able to reach certain tissue in a body of a patient. Accordingly, a surgeon may have to change instruments for different cutting and/or coagulation applications. In addition, the surgical apparatus may not be suitable for certain procedures. This can detract from convenient use of the instrument.

SUMMARY OF THE INVENTION

In view of the above, an ultrasonic surgical apparatus is provided to permit selective cutting, coagulation, and/or clamping of tissue during surgical procedures. In order to promote convenient and efficient use of the apparatus, the surgical apparatus permits the end-effector to be angularly positioned or adjusted with respect to the housing of the surgical apparatus to allow the distal end of the end-effector to reach desired areas within a patient's body. The angularly positionable end-effector provides the surgical apparatus with an increased range of mobility to allow a surgeon to perform various surgical procedures.

The increased range of mobility can be achieved by forming one or more pivoting joints in the elongated portion of the instrument to allow angular motion of the elongated portion. As a result, the end-effector can be adjusted to a desired angular position relative to the housing. The end-effector may be adjusted into an angular position prior to use, or the end-effector may be configured at various angular positions after the end-effector has been inserted through a tube of a trocar or an incision of a patient. This permits the surgeon to access body tissue which may otherwise be difficult to reach.

The end-effector of the apparatus can be selectively rotationally positioned with respect to the housing, thus permitting a surgeon to selectively position the end effector as may be required without effecting rotational manipulation of the housing. The end-effector may be rotatable as a unit, together with a clamping mechanism of the apparatus, relative to the housing. Efficient and convenient use is promoted by the provision of a detent mechanism which functions to provide indexed rotational positioning of the end-effector and/or waveguide with respect to the housing. The waveguide may remain stationary while the end-effector is rotated with respect to the waveguide.

In accordance with the illustrated embodiment, the present ultrasonic surgical apparatus includes a housing which preferably includes a hand grip portion. The apparatus further includes an elongated portion (which may be configured for endoscopic use), including a outer sheath having a proximal end rotatably joined to the housing and a distal end positionable at the region at which tissue cutting, coagulation, and/or clamping is to be effected In the preferred embodiment, a rotational knob is mounted on the outer sheath for effecting indexed rotation of the outer sheath with respect to the housing.

An inner actuating member can be reciprocatably positioned within the outer sheath and can be operatively connected with the outer sheath for rotation therewith with respect to the housing. Reciprocation of the actuating member effects the desired operation of a clamping mechanism of the surgical apparatus provided at the distal end of the outer sheath.

An ultrasonic waveguide is positioned within and extends the length of the outer sheath. The ultrasonic waveguide includes an end-effector at the distal end thereof, with the end-effector extending distally of the distal end of the outer sheath. The end-effector, sometimes referred to as a "blade", is ultrasonically driven by a transducer of an associated ultrasonic drive unit so that longitudinal ultrasonic vibration of the end-effector effects the desired tissue cutting and coagulation. The waveguide and drive unit are preferably joined for rotation with the outer sheath.

The surgical apparatus also includes a mechanism for angularly moving the end effector with respect to the housing. In accordance with the illustrated embodiment, the mechanism includes a drive gear operatively connected to a pivoting gear. The drive gear engages the pivoting gear so that rotational movement of an articulation knob acts to pivot the pivoting gear. The pivoting gear reciprocates a pair of cables for effecting articulation of the elongated portion to angularly position the end-effector relative to the housing.

A clamping mechanism of the surgical apparatus includes a clamp arm pivotally mounted on the distal end of the outer sheath for pivotal movement with respect to the end-effector. Tissue is clamped between the clamp arm and the end-effector, thereby ultrasonically coupling the tissue with the end-effector (when energized) or permitting grasping and clamping of tissue when ultrasonic energy is not being transmitted through the waveguide to the end-effector. The clamp arm is operatively connected to the reciprocable actuating member of the surgical apparatus so that reciprocable movement of the actuating member pivotally moves the clamp arm with respect to the end-effector.

Selective operation of the clamping mechanism is provided by an operating lever pivotally connected to the housing. In the preferred embodiment, the operating lever and associated handgrip portion of the housing are provided with a scissor-like configuration, thus permitting convenient movement of the operating lever by a user's thumb. The operating lever is interconnected with the reciprocable actuating member by a clamp drive mechanism so that pivotal movement of the operating lever reciprocably moves the actuating member for pivotally moving the clamp arm of the surgical apparatus.

The clamp drive mechanism also functions to permit rotation of the actuating member, as well as the outer sheath and the waveguide, relative to the housing. In a presently preferred embodiment, such rotation is indexed to permit the end-effector and the clamping mechanism of the surgical apparatus to be selectively rotatably positioned with respect to the housing at any of a plurality of relative angular dispositions. In accordance with the illustrated embodiment, the drive mechanism interconnects the operating lever and the actuating member. The drive member includes a drive yoke operatively connected to the operating lever, and a drive collar mounted on the actuating member for conjoint rotation therewith. The drive yoke engages the drive collar so that pivotal movement of the operating lever and drive yoke act to reciprocate the drive collar and actuating member.

The invention, together with attendant features and advantages, will best be understood by reference to the following detailed description of the preferred embodiments of the invention, taken in conjunction with the accompanying drawings. It is to be understood that both the foregoing general description and the following detailed description are exemplary and explanatory and are intended to provide further explanation of the invention as claimed.

BRIEF DESCRIPTION OF THE DRAWINGS

FIG. 2 is a side elevational view, partially in cut-away of the clamp coagulator apparatus embodying the principles of the present invention, shown in operative association with an ultrasonic drive unit of the surgical system shown in FIG. 1;

FIG. 3 is an exploded prospective view of the ultrasonic clamp coagulator apparatus of FIG. 1;

FIG. 4 is a fragmentary partial cross-sectional view of a pivoting joint of a waveguide of the clamp coagulator apparatus of FIG. 1;

FIG. 5 is a partial side elevational view of another ultrasonic surgical system including an ultrasonic clamp coagulator apparatus embodying the principles of the present invention;

FIG. 6 is a fragmentary side elevational view of a section of a waveguide of the clamp coagulator apparatus of FIG. 5;

FIG. 10 is a partial side elevational view of another ultrasonic surgical system;

FIG. 11 is a fragmentary perspective view of the distal end of an elongated portion of the surgical system of FIG. 10;

FIG. 12 is a fragmentary side view of the elongated portion of the surgical system of FIG. 10 illustrating the movement of the elongated portion;

FIG. 13 is a partial side view of another embodiment of a surgical system; and

FIG. 14 is a fragmentary partial cross-sectional view of an elongated portion of the surgical system of FIG. 13.

DESCRIPTION OF THE PREFERRED EMBODIMENTS

Figure 1:
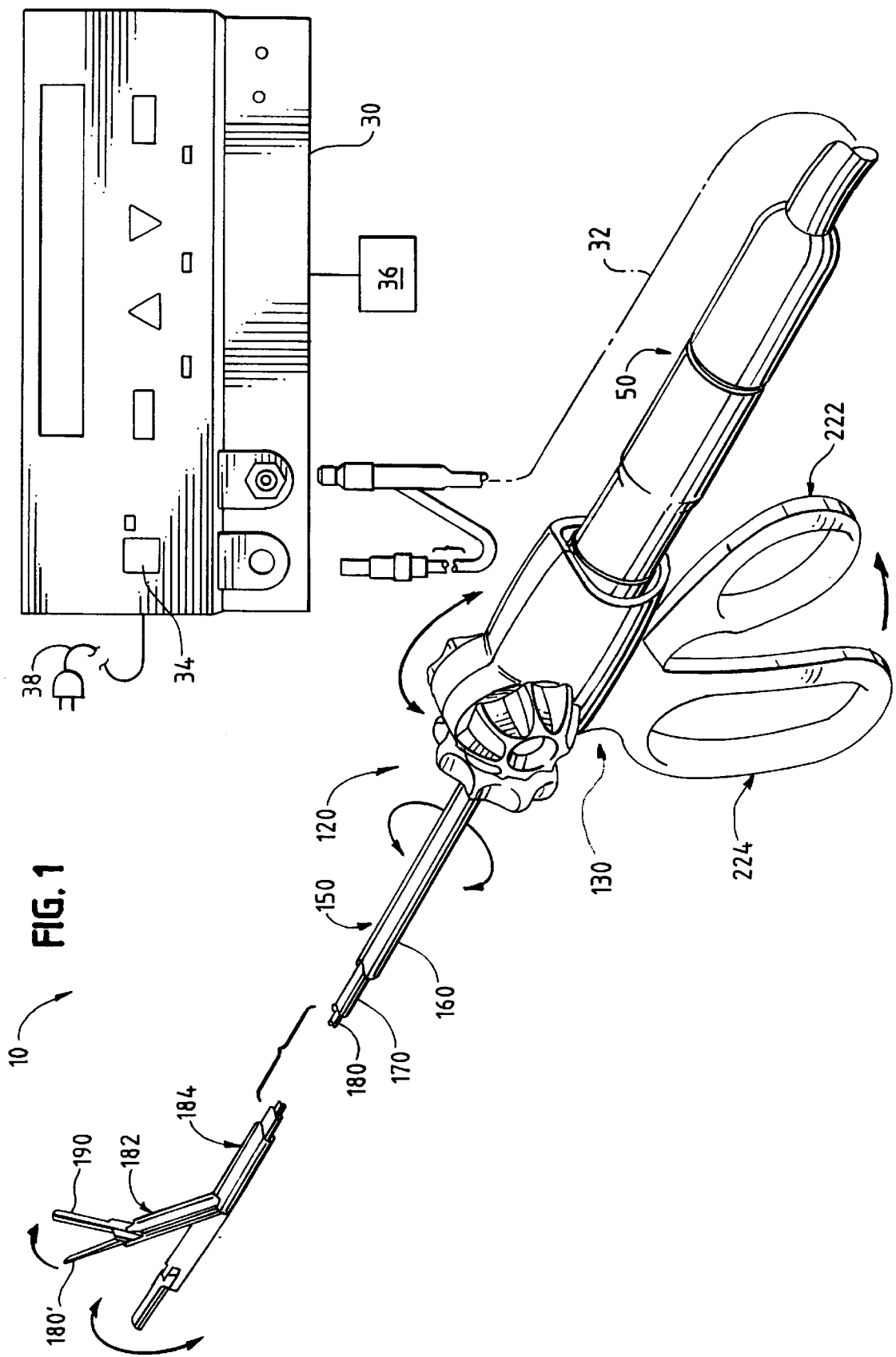
FIG. 1 is a perspective view of an ultrasonic surgical system including an ultrasonic clamp coagulator apparatus embodying the principles of the present invention.

While the present invention is susceptible of embodiments in various forms, there is shown in the drawings and will hereinafter be described a presently preferred embodiment, with the understanding that the present disclosure is to be considered as an exemplification of the invention, and is not intended to limit the invention to the specific embodiment illustrated.

The present invention is particularly directed to an improved ultrasonic surgical clamp coagulator apparatus which is configured for effecting tissue cutting, coagulation, and/or clamping during surgical procedures. The present apparatus can readily be configured for use in both open surgical procedures, as well as laparoscopic or endoscopic procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic "blade" or end-effector of the device.

As will become apparent from the following description, the present clamp coagulator apparatus is particularly configured for disposable use by virtue of its straightforward construction. As such, it is contemplated that the apparatus be used in association with an ultrasonic drive unit of a surgical system, whereby ultrasonic energy from the drive unit provides the desired ultrasonic actuation of the present clamp coagulator apparatus. It will be appreciated that the clamp coagulator apparatus embodying the principles of the present invention can be configured for non-disposable use, and non-detachably integrated with the associated ultrasonic drive unit. However, detachable connection of the present clamp coagulator apparatus with the associated ultrasonic drive unit is presently preferred for single-patient use of the apparatus.

Referring now to FIGS. 1 and 2, therein is illustrated a presently preferred embodiment of a surgical system, generally designated 10, which includes an ultrasonic clamp coagulator apparatus embodying the principles of the present invention. Preferred details of the ultrasonic generator and associated ultrasonic drive unit of the surgical system 10 will first be described, with subsequent detailed description of the ultrasonic surgical clamp coagulator apparatus, including a waveguide configured for articulation and indexed rotation, embodying the principles of the present invention.

The surgical system 10 includes an ultrasonic generator 30 and an associated ultrasonic surgical instrument. The surgical instrument includes an ultrasonic drive unit, designated 50, and an ultrasonic clamp coagulator apparatus 120 embodying the principles of the present invention. As will be further described, an ultrasonic transducer of the drive unit 50, and an ultrasonic waveguide of the clamp coagulator 120, together provide an acoustic assembly of the present surgical system, with the acoustic assembly providing ultrasonic energy for surgical procedures when powered by generator 30. It will be noted that in some applications, the ultrasonic drive unit 50 is referred to as a "hand piece assembly" because the surgical instrument of the surgical system is configured such that a surgeon grasps and manipulates the ultrasonic drive unit 50 during various procedures and operations. The clamp coagulator apparatus 120 embodying the principles of the present invention preferably includes a scissors-like grip arrangement which facilitates positioning and manipulation of the instrument apart from manipulation of the ultrasonic drive unit 50.

The generator 30 of the surgical system sends an electrical signal through a cable 32 at a selected excursion, frequency, and phase determined by a control system of the generator 30. As will be further described, the signal causes one or more piezoelectric elements of the acoustic assembly of the surgical instrument to expand and contract, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. An end-effector at the distal end of the waveguide of the acoustic assembly is placed in contact with tissue of the patient to transfer the ultrasonic energy to the tissue. As further described below, a surgical tool, such as, a jaw or clamping mechanism, is preferably utilized to press the tissue against the end-effector.

As the end-effector couples with the tissue, thermal energy or heat is generated as a result of friction, acoustic absorption, and viscous losses within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end-effector, the frequency of vibration, the amount of pressure applied by the user, the sharpness of the end-effector, and the coupling between the end-effector and the tissue.

As illustrated in FIG. 1, the generator 30 includes a control system integral with the generator 30, a power switch 34, and a triggering mechanism 36. The power switch 34 controls the electrical power to the generator 30, and when activated by the triggering mechanism 36, the generator 30 provides energy to drive the acoustic assembly of the surgical system 10 at a predetermined frequency and to drive the end-effector at a predetermined excursion level. The generator 30 drives or excites the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly including the tissue load. In addition, a second feedback loop in the control system maintains the electrical current supplied to the acoustic assembly at a preselected constant level in order to achieve substantially constant excursion at the end-effector of the acoustic assembly.

The electrical signal supplied to the acoustic assembly will cause the distal end of the waveguide, i.e., the end-effector, to vibrate longitudinally in the range of, for example, approximately 20 kHz to 250 kHz, and preferably in the range of about 54 kHz to 56 kHz, and most preferably at about 55.5 kHz. The excursion of the vibrations at the end-effector can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 preferably comprises a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electrosurgical unit or conventional electrical outlet. It is contemplated that the generator 30 can also be powered by a direct current (DC) source, such as a battery. The generator 30 can comprise any suitable generator, such as Model No. GEN01, available from Ethicon Endo-Surgery, Inc.

As shown in FIGS. 1 and 2, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator 120 principally be grasped and manipulated by a scissors-like arrangement provided by a housing of the apparatus, as will be described below. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by the cable 32. The cable 32 preferably includes ducts or vents 62 to allow air to be introduced into the housing 52 of the ultrasonic drive unit 50 to cool the transducer assembly 40 of the acoustic assembly.

The housing 52 of the ultrasonic drive unit 50 is preferably constructed from a durable plastic, such as Ultem®. It is also contemplated that the housing 52 may alternatively be made from a variety of materials including other plastics (i.e., liquid crystal polymer (LCP), nylon, or polycarbonate), or metallic materials. A suitable ultrasonic drive unit 50 is Model No. HP050, available from Ethicon Endo-Surgery, Inc.

As shown in FIG. 2, the acoustic portion includes the transducer stack or assembly 40 a mounting device 84, and a transmission component or working member, referred to herein as a waveguide having an end-effector. The transducer assembly 40 and mounting device 84 are preferably carried by the ultrasonic drive unit 50, and the waveguide is carried by the ultrasonic clamp coagulator apparatus.

The components of the acoustic assembly are preferably acoustically tuned such that the length of each component is an integral number of one-half wavelengths (n$\lambda$/2), where the wavelength $\lambda$ is the wavelength of a preselected or operating longitudinal vibration frequency $f_0$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end-effector at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda$/4).

As shown in FIG. 2, the transducer assembly 40 of the acoustic assembly, which is also known as a "Langevin stack", generally includes a transduction portion 90, a first resonator 92, and a second resonator 94. The transducer assembly is preferably an integral number of one-half system wavelengths (n$\lambda$/2) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of material used in the resonators 92 and 94, and the desired fundamental frequency $f_0$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 preferably comprises a piezoelectric section of alternating positive electrodes 96 and negative electrodes 98, with piezoelectric elements 100 alternating between the electrodes 96 and 98. The piezoelectric elements 100 can be fabricated from any suitable material, such as, for example, lead zirconate-titanate, lead metaniobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to electrodes 96 and 98.

As illustrated in FIG. 2, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94. The bolt can be fabricated from steel, titanium, aluminum, or other suitable material and is preferably fabricated from Ti-6Al-4V Titanium, and most preferably from 4037 low alloy steel.

The piezoelectric elements 100 are energized in response to the electrical signal supplied from the generator 30 to produce an acoustic standing wave in the acoustic assembly. The electrical signal causes an electro-magnetic field across the piezoelectric elements 100, causing the piezoelectric elements 100 to expand and contract in a continuous manner along the axis of the voltage gradient, producing high frequency longitudinal waves of ultrasonic energy. The ultrasonic energy is transmitted through the acoustic assembly to the end-effector.

The mounting device 84 of the acoustic assembly has a proximal end, a distal end, and preferably has a length substantially equal to an integral number of one-half system wavelengths. The proximal end of the mounting device 84 is preferably axially aligned and coupled to the distal end of the second resonator 94 by an internal threaded connection near an anti-node. (For purposes of this disclosure, the term "near" is defined as "exactly at" or "in close proximity to".) It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 preferably includes an integral mounting flange 108 disposed around its periphery. The mounting flange 108 is preferably disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 86 to reduce or prevent ultrasonic vibration from being transmitted from the mounting device 84 to the housing 52.

The mounting device 84 is preferably secured in a predetermined axial position by a plurality of pins 114, preferably four. The pins 114 are disposed in a longitudinal direction ninety (90) degrees apart from each other around the outer periphery of the mounting device 84. The pins 114 are coupled to the housing 52 of the ultrasonic drive unit 50 and are disposed through notches in the acoustic mounting flange 108 of the mounting device 84. The pins 114 are preferably fabricated from stainless steel.

The mounting device 84 is preferably configured to amplify the ultrasonic vibration excursion that is transmitted through the acoustic assembly to the distal end of the end-effector. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 be configured as any suitable shape, such as, for example, a stepped horn, a conical horn, an exponential horn, a unitary gain horn, or the like.

As shown in FIG. 2, the mounting device 84 is preferably acoustically coupled to the waveguide of the ultrasonic clamp coagulator apparatus 120. The distal end of the mounting device 84 is preferably coupled to the proximal end of the waveguide by an internal threaded connection near an anti-node, but alternative coupling arrangements can be employed. For example, a ball and socket arrangement, as described below, and as shown in co-pending application Ser. No. 08/770,550, filed Dec. 23, 1996, hereby incorporated by reference, may be employed to allow the proximal end of the waveguide to interface with the distal end of the mounting device, thus permitting ultrasonic energy to pass therethrough. This ball and socket arrangement allows the clamp coagulator apparatus 120 to be quickly attached to the drive unit 50 and detached from the drive unit 50.

Referring now to FIG. 3, an exploded view of the ultrasonic clamp coagulator apparatus 120 of the surgical system 10 in accordance with a preferred embodiment is illustrated. The proximal end of the ultrasonic clamp coagulator apparatus 120 preferably receives and is fitted to the distal end of the ultrasonic drive unit 50 by insertion of the drive unit into the housing of the apparatus, as shown in FIG. 1. The ultrasonic clamp coagulator apparatus 120 is preferably attached to and removed from the ultrasonic drive unit 50 as a unit. The ultrasonic clamp coagulator 120 may be disposed of after a single use.

The ultrasonic clamp coagulator apparatus 120 preferably includes a handle assembly or a housing 130, preferably comprising mating housing portions 131, 132, and an elongated or endoscopic portion 150. When the present apparatus is configured for endoscopic use, the construction can be dimensioned such that the elongated portion 150 has an outside diameter of about 5.5 mm. The elongated portion 150 of the ultrasonic clamp coagulator apparatus 120 extends orthogonally from the apparatus housing 130 and includes an articulating section.

The articulating section of the elongated portion 150 may be selectively moved or adjusted by a surgeon to a desired angle relative to the housing 130. The articulating portion provides the surgeon with an increased range of operability to perform various surgical procedures. The increased range of operability is achieved through a pivoting joint or section in the endoscopic portion 150. It is contemplated that the endoscope portion 150 may have any suitable number of articulable sections. The elongated portion can also be selectively rotated with respect to the housing 130 as further described below.

As shown in FIG. 3, the elongated portion 150 preferably includes an outer tubular member or sheath 160, an inner tubular actuating member 170, and a waveguide 180 having an end-effector 180'. The outer tubular member preferably includes an articulating or movable portion 182 and non-articulating portion 184. The distal end of the non-articulating portion 184 has a pair of lugs 186 and 188, each defining a bore. The bores are aligned transversely and define a pivot axis or articulation axis 190 about which the articulating portion 182 of the outer tubular member pivots or articulates. The proximal end of the articulating portion 182 has a pair of mating lugs 192 and 194, each having an outwardly projecting pin for being received in the respective bore of the lugs 186 and 188.

The tubular actuating member 170 also preferably includes an articulating or movable portion and non-articulating portion. An articulable connection between the articulating and non-articulating portions of the actuating member is provided. An integral "living hinge" connection is provided by configuring the actuating member to include a relatively narrow, flexible portion extending between the spaced apart articulating and non-articulating portions of the actuating member 170. Axial translation of the non-articulating portion is thus transmitted to the articulating portion, while accommodating relative articulation. Alternatively, a bellows mechanism can be provided to operatively connect the articulating and non-articulating portions of the actuating member.

The proximal end of the waveguide 180 is preferably coupled to the mounting device 84 of the ultrasonic drive unit 50 near an anti-node as described above. The waveguide 180 preferably includes an articulating portion 195 and a non-articulating portion 196. As shown in FIG. 4, the distal end of the non-articulating portion 196 of the waveguide preferably has a mating or coupling surface that mates with a mating or coupling surface of the proximal end of the articulating portion 195. The mating surface of the distal end of the non-articulating portion 196 preferably has a non-threaded cavity or bore 197 that is substantially conically concave or wedge shaped. It is also contemplated that the mating surface of the distal end of the non-articulating portion 196 can be formed as a convex or partially curved surface, or any other suitable shape.

The mating surface of the proximal end of the articulating portion 195 has a non-threaded axially extending member or projection 198 as shown in FIG. 4. The mating surface is preferably substantially spherically or cylindrically shaped. It will be recognized that any suitable mating surface could be used without departing from the spirit and scope of the present invention. It is also contemplated that the mating surfaces of the articulating and non-articulating portions could be interchanged.

Figure 9:
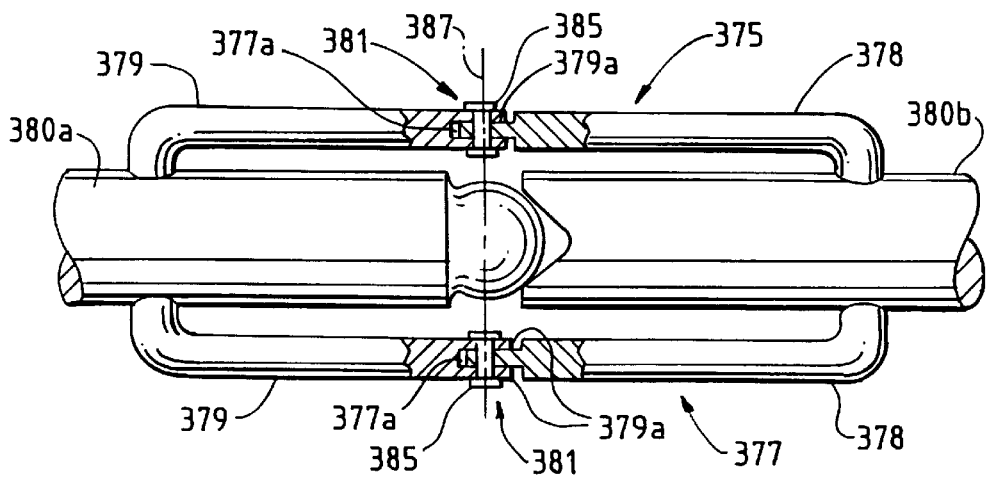
FIG. 9 is a fragmentary top view, partially in cut-away of the two segments of the waveguide of FIG. 8.

The mating surfaces of the articulating portion 195 and non-articulating portions 196 of the waveguide 180 are held together by fixed or spring-loaded members that are attached to the waveguide at nodes so that the junction or point of contact is preferably near an antinode (see FIG. 9). The mating surfaces provide a socket arrangement or a pivotal joint to allow the articulating portion of the waveguide to be angularly moved with respect to the non-articulating portion and to permit ultrasonic energy to pass therethrough. The mating surfaces of the waveguide 180 can be coated with titanium nitride (TiN) or another suitable material to improve wear life.

The waveguide 180 preferably has a length substantially equal to an integer number of one-half system wavelengths $(n\lambda/2)$. The waveguide 180 is preferably fabricated from a solid core shaft constructed out of material which propagates ultrasonic energy efficiently, such as titanium alloy (i.e., Ti-6Al-4V) or an aluminum alloy (i.e., 7075). It is contemplated that the waveguide 180 can alternatively be fabricated from any other suitable material and can have a hollow core.

The waveguide 180 is preferably substantially semi-flexible. It will be recognized that the waveguide 180 can alternatively be substantially rigid. The waveguide 180 may be configured to amplify the mechanical vibrations transmitted through the waveguide 180 to the end-effector as is well known in the art. The waveguide 180 may further have features to control the gain of the longitudinal vibration along the waveguide 180 and features to tune the waveguide 180 to the resonant frequency of the system. It will be recognized that the waveguide 180 may have any suitable cross-sectional dimension. For example, the waveguide may have a substantially uniform cross-section or the waveguide 180 may be tapered at various sections or may be tapered along its entire length.

The waveguide 180 preferably includes at least one radial hole or aperture (not shown) extending diametrically therethrough, substantially perpendicular to the axis of the waveguide 180. The aperture is preferably positioned at a node, but may be otherwise positioned. The aperture is configured to receive a connector pin member (not shown) which connects the waveguide 180, the tubular actuating member 170, and the tubular outer sheath 160 together for conjoint, indexed rotation relative to apparatus housing 130.

The waveguide 180 may also have a plurality of grooves or notches (not shown) formed in its outer circumference. The grooves may be located at nodes of the waveguide 180 to act as alignment indicators for the installation of a damping sheath (not shown) and stabilizing silicone rings or compliant supports during manufacturing. A seal is preferably provided at the distal-most node, nearest the end-effector 180', to abate passage of tissue, blood, and other material into the region between the waveguide 180 and actuating member 170.

The end-effector 180' is preferably integral therewith and formed as a single unit. The end-effector 180' may alternately be connected to the waveguide 180 by a threaded connection, by a welded joint, or by a pivotal joint as described above. The distal end of the end-effector 180' is disposed near an anti-node in order to tune the acoustic assembly to a preferred resonant frequency $f_o$ when the acoustic assembly is not loaded by tissue. When the transducer assembly is energized, the distal end of the end-effector 180' is configured to move longitudinally in the range of, for example, approximately 10–500 microns peak-to-peak, and preferably in the range of about 10 to about 100 microns at a predetermined vibrational frequency $f_o$, preferably at 55,500 Hz.

The end effector 180' can have a length substantially equal to an integral multiple of one-half system wavelengths ($n\lambda/2$). The distal end of the end effector 180' is disposed at (or in close proximity to) an antinode in order to produce the maximum longitudinal deflection of the distal end. When the transducer assembly is energized, the distal end of the end effector 180' is configured to move longitudinally in the range of, for example, approximately 10 to 500 microns peak-to-peak, and preferably in the range of about 30 to 100 microns at a predetermined vibrational frequency, and most preferably at about 65–90 microns.

The end effector 180' is preferably made from a solid core shaft constructed of material which propagates ultrasonic energy, such as a titanium alloy (i.e., Ti-6Al-4V) or an aluminum alloy. It will be recognized that the end effector 180' can be fabricated from any other suitable material. It is also contemplated that the end effector 180' may have a surface treatment to improve the delivery of energy and desired tissue effect. For example, the end effector 180' may be micro-finished, coated, plated, etched, grit-blasted, roughened or scored to enhance coagulation in tissue and/or reduce adherence of tissue and blood to the end effector. Additionally, the end effector 180' can be sharpened or shaped to enhance its energy transmission characteristics. For example, the end effector 180' may be blade shaped, hook shaped, or ball shaped. The end-effector 180', sometimes referred to as a blade, can also be cylindrical for cooperation with the associated clamping mechanism of the present clamp coagulator apparatus. The end-effector may also receive suitable surface treatment, as is known in the art.

The end effector 180' can have a distal region having a smaller cross-section area than a proximal region thereof, thereby forming a vibrational amplitude step-up junction. The step-up junction acts as velocity transformer as known in the art, increasing the magnitude of the ultrasonic vibration transmitted from the proximal region to the distal region of the end effector 180'.

As shown in FIG. 3, the surgical instrument 120 further includes a mechanism 140 to move or adjust the articulating section of the endoscopic portion 150 to a desired angular position with respect to the handle assembly 130. The mechanism 140 preferably includes articulating knobs 141 and 142, a drive gear or wheel 143, a pivoting or ball gear 144, and one or more rods or wires 145 and 146 (two being shown). The articulating section of the elongated portion 150 may be selectively moved by turning either of the knobs 141 and 142.

The knob 141 is mounted for rotation on the housing portion 131 of the handle assembly 130 about an axis extending perpendicularly to, but spaced from, the longitudinal axis of the non-articulable components of elongated portion 150. The knob 142 is also mounted for rotation on the housing portion 132 of the handle assembly 130. The knob 141 includes a shaft 147 projecting from its center and the knob 142 is mounted on the opposite end of the shaft 147.

The drive gear 143 is mounted to the shaft 147 to control the articulation of the elongated portion 150. The drive gear 143 preferably includes a plurality of teeth to engage one or more grooves formed in the pivoting gear 144 which is pivotally mounted to the waveguide by, for example, a pin 244. The pivoting gear 144 has a plurality of grooves extending around its circumference. Thus, when the elongated portion 150 is rotated, the pivoting gear 144 rotates while allowing the teeth of the drive gear 143 to remain in engagement with the grooves of the pivoting gear 144.

The pin 212 is preferably disposed through an aperture extending diametrically through the waveguide 180 at a node. The pin 212 connects the waveguide 180, the actuating member 170, and the pivoting gear 144 for rotation together, while accommodating the necessary relative axial movement of these components. The 212 pin allows the pivoting gear 144 to pivot about on an axis 148 to move the wires 145 and 146 in a longitudinal direction as further described below. The wires 145 and 146 may be fabricated from any suitable materials, such as, for example, steel alloys, titanium, or the like.

The distal end of the wires 145 and 146 are attached to the proximal end of the articulating portion 182 of the outer sheath 180. The wires 145 and 146 can be attached to the outer sheath 180 by any suitable means. The proximal ends of the wires 145 and 146 are attached to the distal end of the pivoting gear 144. When the pivoting gear 144 pivots about the axis 148, the wires 145 and 146 move in a direction perpendicular to the longitudinal axis of the waveguide 180.

To pivot the articulating section of the elongated portion 150 with respect to the handle assembly 130 of the surgical apparatus, one of the articulating knobs 141 and 142 can be rotated. When the knobs 141 and 142 are rotated in the direction of arrow $A_1$, the pivoting gear 144 pivots to exert tension on and move the wire 146 rearwardly resulting in angular movement of the articulating section of the elongated portion 150 in the direction of arrow $A_2$ as shown in FIG. 3, and forward movement of wire 145. When the knobs 142 and 144 are rotated in the opposite direction of arrow $A_1$, the pivoting gear 144 pivots to tension and move the wire 145 rearwardly while the wire 146 moves forwardly resulting in articulation of the articulating section of the elongated portion 150 in the opposite direction of arrow $A_2$.

Referring still to FIG. 3, reciprocable movement of the actuating member 170 to actuate the clamp mechanism is effected by the provision of a drive collar, generally designated 200, mounted on the proximal end of the actuating member for conjoint rotation. To this end, the drive collar includes a pair of diametrically opposed axially extending arms 202 each having a drive lug (not shown), with the drive lugs being biased by the arms 202 into engagement with suitable openings defined by the proximal portion of the actuating member 170. Rotation of the drive collar 200 together with the actuating member 170 is further effected by the provision of a pair of keys (not shown) diametrically engageable with suitable openings defined by the proximal end of the actuating member 170.

Rotation of the actuating member 170 together with tubular outer sheath 160 and inner waveguide 180 is provided by the connector pin 212 extending through these components of the apparatus. The tubular actuating member 170 defines an elongated slot (not shown) through which the connector pin 212 extends to accommodate reciprocable movement of the actuating member relative to the outer tubular sheath and inner waveguide.

A rotation knob 216 mounted on the outer tubular sheath facilitates rotational positioning of the elongated portion 150 with respect to the handle assembly 130 of the clamp coagulator apparatus. The connector pin 212 preferably joins knob 216 together with sheath 160, member 170, and waveguide 180 for rotation as a unit relative to handle assembly 130. In a current embodiment, hub portion 216' of the rotation knob acts to rotatably mount the outer sheath 160, the actuating member 170, and the waveguide 180 (as a unit with knob 216), on the housing 130.

In accordance with the present invention, the drive collar 200 provides a portion of the clamp drive mechanism of the apparatus which effects pivotal movement of the clamp arm 190 by reciprocation of the actuating member 170. The clamp drive mechanism further includes a drive yoke 220 which is operatively connected with an operating lever 222 of the apparatus, with the operating lever thus interconnected with the reciprocable actuating member 170 via the drive yoke 220 and the drive collar 200. The operating lever 222 is pivotally connected to the handle assembly 130 of the apparatus for cooperation in a scissors-like fashion with a handgrip portion 224 of the handle assembly. Movement of the lever 222 toward handgrip portion 224 translates the actuating member 170 proximally, thereby pivoting the clamp arm 190 toward the end-effector 180'.

Operative connection of the drive yoke 220 with the operating lever 222 is provided by a spring 226, preferably comprising a compression coil spring. The spring 226 fits within a spring slot 228 defined by the drive yoke 220, which in turn is positioned between a pair of spring retainer flanges 230 of the operating lever 222. The drive yoke 220 is pivotally movable with respect to the spring flanges 230 in opposition to the compression coil spring, which bears against the surfaces of the spring slots defined by each of the spring flanges 230. In this manner, the force which can be applied to the actuating member 170, by pivotal movement of operating lever 222 acting through drive yoke 220 and drive collar 200, is limited by the force with which the spring 226 bears against the spring flanges 230. Application of excessive force results in pivotal displacement of the drive yoke 220 relative to the spring flanges 230 of the operating lever 222 in opposition to spring 226. In a presently preferred embodiment, the spring 226 is selected to limit clamping force at clamp arm 190 to approximately 2 pounds. The handle assembly 130 can have stop portions (not shown) to limit the travel of the operating lever 222 to prevent excessive compression of the spring 226.

In accordance with the present invention, indexed rotational positioning of the elongated portion 150 of the present clamp coagulator apparatus 120 is provided by the provision of a detent mechanism incorporated into the clamp drive mechanism of the apparatus. Specifically, the drive collar 200 includes a pair of axially spaced apart drive flanges 232. A detent-receiving surface is provided between the drive flanges 232, and defines a plurality of circumferentially spaced teeth which define detent-receiving depressions generally about the periphery of the drive collar 200. In a presently preferred embodiment, twelve (12) of the teeth are provided, thereby providing indexed positioning of the elongated portion 150 of the apparatus at 30° intervals relative to the housing 130 of the apparatus.

Indexed rotational movement is further achieved by the provision of at least one, and preferably a pair, of diametrically opposed detents 236 respectively provided on cantilevered yoke arms 238 of the drive yoke 220. By this arrangement, the yoke arms 238 are positioned between the drive flanges 232 for engagement with the confronting surfaces thereof, and bias the detents 236 into engagement with the drive collar 200. Indexed relative rotation is thus achieved, with the detents 236 of the yoke arms cooperating with the drive flanges 238 for effecting reciprocation of the actuating member 170. In a presently preferred embodiment, the drive yoke 220 is formed from suitable polymeric material, with the biasing force created by the yoke arms acting on the detents thereof cooperating with the radial depressions defined by the drive collar to resist relative rotational torque less than about 1 to 2 inch-pounds. As such, the elongated portion 150 of the clamp coagulator apparatus is maintained in any of its selected indexed rotational positions, relative to housing 130, unless a torque is applied (such as by the rotation knob 216) exceeding this predetermined torque level. A snap-like indexing action is thus provided.

Rotation of the elongated portion 150 of the present clamp coagulator apparatus 120 can be effected together with relative rotational movement of ultrasonic drive unit 50 with respect to apparatus handle assembly 130. If a threaded connection is provided to join the elongated portion 150 to the ultrasonic drive unit 50 in ultrasonic-transmitting relationship, the proximal portion of the outer tubular sheath 160 is preferably provided with a pair of wrench flats. The wrench flats allow torque to be applied by a suitable torque wrench or the like to thereby permit the waveguide 180 to be joined to the ultrasonic drive unit 50. Alternatively, a ball and socket connection can be provided for operatively coupling the elongated portion 150 to the ultrasonic drive unit 50, thus obviating the need for wrench flats or the like. The ultrasonic drive unit, as well as the elongated portion 150, are thus rotatable, as a unit, by suitable manipulation of rotation knob 216, relative to housing 130 of the apparatus. The interior of handle assembly 130 is dimensioned to accommodate such relative rotation of the drive unit 50. Alternatively, the elongated portion 150 of the clamp coagulator apparatus 120 can be rotated while the ultrasonic drive unit 50 remains stationary when a ball and socket arrangement is provided at the junction of the distal end of the mounting device and the proximal end of the waveguide 180 as described above.

The clamping mechanism of the clamp coagulator apparatus 120 is configured for cooperative action with the end-effector 180' of the waveguide 180. The clamping mechanism includes a pivotally movable clamp arm 190, which is pivotally connected at the distal end thereof to the distal end of outer tubular sheath 160. A clamp pad (not shown), preferably formed from Teflon or other suitable low-friction material, is mounted on the surface of the clamp arm for 190 cooperation with the end-effector 180', with pivotal movement of the clamp arm 190 positioning the clamp pad in substantially parallel relationship to, and in contact with, the end-effector 180'. By this construction, tissue to be clamped is grasped between the pad and the end effector 180'. As illustrated, the pad is preferably provided with a sawtooth-like configuration to enhance the gripping of tissue in cooperation with the end-effector 180'.

Pivotal movement of the clamp arm 190 with respect to the end-effector is effected by the provision of at least one, and preferably a pair of lever portions 190' of the clamp arm 190 at the proximal end thereof. The lever portions are positioned on respective opposite sides of the waveguide 180 and end-effector 180', and are in operative engagement with a drive portion of the reciprocable actuating member 170. Reciprocable movement of the actuating member, relative to the outer tubular sheath 160 and the waveguide 180, thereby effects pivotal movement of the clamp arm 190 relative to the end-effector. The lever portions 190' can be respectively positioned in a pair of openings defined by the drive portion, or otherwise suitably mechanically coupled therewith, whereby reciprocable movement of the actuating member acts through the drive portion and lever portions 190' to pivot the clamp arm 190.

Referring now to FIG. 5, another surgical system, generally designated 300, embodying the principles of the present invention is illustrated. The surgical system 300 includes an ultrasonic clamp coagulator apparatus 320 and a drive unit 330, which in many respects correspond in construction and function to the previous described clamp coagulator apparatus 120 and drive unit 50 of FIG. 1 except that the elongated portion 350 of the clamp coagulator apparatus 320 has a plurality of articulating sections. Components of the surgical system 300 which generally correspond to like components in the above-described embodiment are designated with like-numerals in the three-hundred series. It will be recognized that the elongated portion 350 may have any suitable number of articulating sections. The elongated portion 350 preferably includes a flexible outer tubular member or sheath 360, and a waveguide 380 having an end-effector 380'.

Referring to FIG. 6, a fragmentary side view of the waveguide 380 of the clamp coagulator apparatus 320 is illustrated. The waveguide 380 preferably includes a plurality of articulating segments or components 380a, 380b and 380c. The distal ends of each of the segments 380a, 380b and 380c of the waveguide 380 each have a mating or coupling surface that mates with a mating or coupling surface of the proximal end of each adjacent segment or component. The mating surfaces of the distal ends of the segments 380a, 380b and 380c may have a non-threaded cavity or bore that is substantially conically concave, or wedge shaped. It is also contemplated that the mating surfaces of the distal ends of the segments may be formed as a convex or partially curved surface.

The mating surfaces of the segments proximal ends of the 380a, 380b and 380c have a non-threaded axially extending member or projection. The mating surfaces of the proximal ends of the segment is preferably substantially spherically or cylindrically shaped. It will be recognized that any suitable mating surfaces could be used without departing from the spirit and scope of the present invention. It is contemplated that the mating surfaces of the proximal ends and distal ends of the segments could be interchanged.

The mating surfaces of the segments 380a, 380b and 380c are maintained together so that the junction or point of contact is preferably near an antinode. The junctions between the segments provide socket arrangements or pivotal joints. The socket arrangements allow the segments of the waveguide 380 to be angularly moved with respect to one another, permitting the waveguide 380 to be configured to a desired shape.

Figure 7:
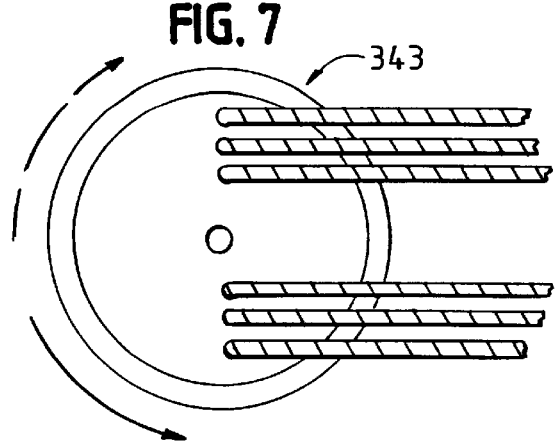
FIG. 7 is an elevational view of an articulation wheel of the clamp coagulator apparatus of FIG. 5.

An articulating mechanism can move or adjust the segments of the waveguide 380 to a desired angular position with respect to the handle assembly 330. The articulating mechanism includes at least one knob 342, a drive wheel 343, and one or more rods or wires 345. As shown in FIG. 7, the proximal end of the wires 345 are connected to the drive wheel 343.

The distal end of the wires can be attached (i.e., welded) to the segments of the waveguide at a node. Preferably, pins extend through the segments at nodes and the distal ends of the wires are attached to the pins. It will be recognized that the wires may be attached to the segments of the waveguide or pins by any suitable means.

The drive wheel 343 can be mounted to a shaft of the articulating knob 342. When the knob 342 is rotated in the direction of arrow $A_3$, the wheel moves the wires to angularly move the elongated portion in the direction of arrow $A_4$ as shown in FIG. 5. When the knob 342 is rotated in the opposite direction of the arrow $A_4$, the elongated portion is articulated in the direction of arrow $A_5$.

Figure 8:
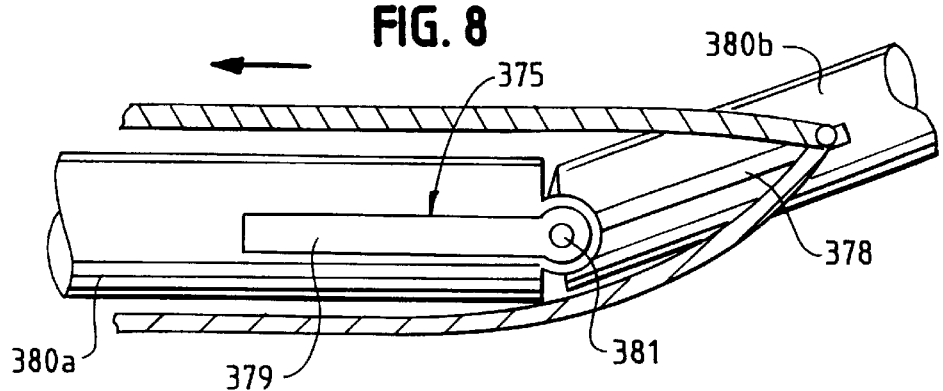
FIG. 8 is a fragmentary side view of a coupling arrangement between two segments of the waveguide of FIG. 5.

As shown in FIGS. 8–9, coupling members 375 and 377 maintain the mating surfaces between the segments 380a and 380b in contact with each other. Each coupling member includes a pair of arms 378 and 379 and a pivoting joint 381. The proximal ends of the arms 379 are connected to the segment 380a of the waveguide at a node and the distal end of the arms 379 have a pair of lugs 379a. Each of the lugs define a bore disposed therethrough.

The distal ends of the arms 379 are connected to the segment 380b of the waveguide at a node and the proximal end of the arms 378 has a mating lug having a bore disposed therethrough. Pins 385 are disposed throughout the bores of the lugs 377a and 379a to couple the arms 378 and 379 together to allow the arms to pivot about an axis 387 defined by the pins.

It is important to note that in the embodiment illustrated in FIGS. 8 and 9, as well as in other embodiments disclosed herein, a spring force is provided to maintain the segments of the waveguide in contact with each other for efficient transmission of ultrasonic energy. This can be achieved by configuring arms 379 to exhibit a desired spring constant, and stretching or elongating the arms during assembly to create the desired spring force. Connecting pins 385 could also be configured to function as springs connecting the proximal and distal portions of the arms, either by configuring the pins as springs, or by providing the pins with an elastomeric coating. By such an arrangement, the pins 385 can be slightly compressed during assembly (in opposition to the spring force) to thereafter provide the necessary force to join the waveguide segments. Formation of an interference fit between the components can also act to provide the necessary coupling force, with use of relatively rigid connecting elements effectively providing the desired spring force.

Referring now to FIGS. 10–12, another surgical system, generally designated 400, embodying the principles of the present invention is illustrated. In many respects, the surgical system 400 corresponds in construction and function to the previous described surgical system 10 except that the drive unit is attached to a different surgical apparatus 410. The surgical apparatus 410 includes a housing 420 and an elongated portion 430. The elongated portion 430 also includes a passive articulating section 460 (i.e., a surgeon has to adjust the articulation of the articulation section by direct manipulation of the section). The elongated portion has an outer tubular member and a waveguide having an end-effector 440' extending therethrough.

The elongated portion 430 of the surgical apparatus 410 preferably includes an articulating or movable portion 460 and non-articulating portion 470. The distal end of the non-articulating portion 470 has a pair of lugs 472 and 474, each defining a bore. The bores are aligned transversely and define a pivot axis or articulation axis 476 about which the articulating portion of the outer tubular member pivots or articulates. The proximal end of the articulating portion 460 has a pair of matting lugs, each having an outwardly projecting pin 478 for being received in the respective bore of the lugs 472 and 474. It is contemplated that the joint between the articulating portion 460 and non-articulating portion 470 comprise a hinge, ball and socket, or any other suitable joint. The joint allows the articulating section to be adjusted or angled with respect to the non-articulating portion 470.

The distal end of the non-articulating portion 470 of the waveguide preferably has a mating or coupling surface that mates with mating or coupling surfaces of the proximal end of the articulating portion 460. The mating surface of the non-articulating section and the mating surface of the articulating section are forced together axially so that the junction or point of contact is preferably near an antinode. The coupling force between the mating surfaces is created by the outer sheath which is attached to the articulating and non-articulating portions of the waveguide at a node.

As shown in FIG. 12, the articulating portion 460 of the elongated portion 430 is pivotally or hingedly mounted to the non-articulating portion 470 of the elongated portion 430. As a result, the end effector 440' can be angularly moved with respect to the housing 420. The elongated portion 430 may also be rotated about a longitudinal axis as indicated by the arrows in FIG. 11. Such rotational motion can be accommodated by the provision of a ball and socket arrangement for operatively coupling segments of the waveguide.

Referring now to FIG. 13, another surgical system, generally designated 500, embodying the principles of the present invention is illustrated. The surgical system 500 includes a ultrasonic surgical apparatus 410 and a drive unit 415, which in many respects correspond in construction and function to the previous described surgical system 400 except that the elongated portion 570 includes a plurality of articulating sections or portions. It will be recognized that the elongated portion 570 may have any suitable number of articulating sections.

As shown in FIGS. 13 and 14, the elongated portion 570 of the surgical apparatus 510 includes a waveguide 580, tension wires 585, and an outer sheath 590. The waveguide 580 preferably includes a plurality of articulating or movable segments or components 580a, 580b and 580c. The distal ends the segments 580a, 580b and 580c preferably have mating or coupling surfaces that mates with mating or coupling surfaces of the proximal ends of adjacent segments or components. The mating surfaces of the segments correspond, in many respects, in construction and function to the previous described mating surfaces of the segments of the waveguide 380 in FIG. 6.

The tension wires 585 of the elongated portion 570 provide a force to create a substantially uniform contact force between the mating surfaces of the segments of the waveguide 580 when tightened. The tension wires can be tightened or loosened through an adjustable tensioner or spring 595 in order to increase or decrease the force applied by the tension wires, allowing the waveguide 580 to be configured in a desired shape. The waveguide can be positioned in a wide range of connected angles with respect to each other.

Thus, the present surgical apparatus are configured for highly efficient and versatile use, with the construction being sufficiently straight-forward and economical in configuration to permit single-patient use. Components of the apparatus can be fabricated from materials suited for surgical applications.

The surgical clamp coagulator apparatus includes an elongated portion that can be selectively moved or articulated to allow the distal end to be oriented at desired angular position. The articulating section provides the surgeon with an increased range of mobility to perform various surgical procedures. The articulating section is achieved through one or more pivoting joints in the elongated portion of the surgical apparatus. The distal end of the instrument may be both articulated in and out of longitudinal alignment with the elongated tubular portion and rotated 360 degrees about the longitudinal axis of the elongated tubular portion. The surgical devices further allow the surgeon to easily adjust the location and angle of the distal end of the elongated portion in order to accurately cut or coagulate body tissue. The elongated portion can be adjusted into a curved angular position prior to use. Alternatively, the elongated portion can be configured at various angular positions after the elongated portion is inserted through a tube of a trocar or in an incision of a patient. This permits the surgeon to gain access to body tissue which may otherwise be difficult to reach.

When a surgeon is ready to use the surgical apparatus, the surgeon simply attaches the surgical apparatus onto the drive unit. Once the surgical apparatus is attached to the drive unit, the surgeon can rotate the articulation knob to adjust the end-effector at a desired angular position and can rotate the rotational knob to rotate the end-effector in order to position the end-effector at a desired rotational position. The end-effector can be adjusted and/or rotated after the end-effector is inserted into a patient. This permits the surgeon to gain access to body tissue which is otherwise difficult to reach. Suitable vibration is then transmitted to the end effector to cut and/or coagulated the desired tissue.

The combination of rotation and articulation allows for considerable flexibility in cutting and coagulating tissue in various surgical procedures, such as, for example, open surgery operations and endoscopic procedures. The surgical devices improve accessibility to tissue within the body of a patient and enable a surgeon to work on tissue located at various angles to the surgical devices.

As will be appreciated, the present instrument is desirably configured such that the instrument is relatively rigid after the desired articulation thereof. In other words, the instrument is not "fully flexible" (such as flexible tubing or the like), but rather is "piece-wise rigid" with articulation joints provided between rigid components. After selected articulation, the instrument is arranged to maintain that configuration until reconfigured by the user. Further versatility of the present instrument is achieved by its utility in an unarticulated, generally linear orientation.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical clamp apparatus comprising:

a housing;

an outer sheath extending from the housing, the outer sheath having at least one articulating portion and a non-articulating portion;

an inner actuating member reciprocably positioned within said outer sheath for rotation therewith with respect to said housing;

an ultrasonic waveguide positioned within said outer sheath and having an end-effector extending distally of the distal end of the outer sheath, the waveguide having at least one articulating portion and a non-articulating portion, the waveguide further adapted to receive a vibrational energy and to propagate the vibrational energy from the non-articulating portion to the articulating portion;

a clamp arm pivotally mounted on the distal end of the outer sheath for pivotal movement with respect to the end-effector for clamping tissue between the clamp arm and the end-effector, the clamp arm being operatively connected to the actuating member so that reciprocable movement of the actuating member pivotally moves the clamp arm with respect to the end-effector;

an operating lever pivotally mounted on said housing, and a clamp drive mechanism interconnecting the operating lever with the actuating member so that pivotal movement of the operating lever reciprocably moves the actuating member for pivotally moving the clamp arm;

an articulating knob coupled to the housing;

and an articulation mechanism cooperating the with the articulating knob to effect articulation of the articulating portion of the outer sheath between a first position where the articulating portion of the outer sheath is disposed at an angle to the non-articulating portion of the outer sheath and a second position where the articulating portion of the outer sheath is substantially coaxial with the non-articulating portion of the outer sheath.

2. The ultrasonic surgical clamp apparatus of claim 1 where the articulation mechanism includes:

a pivoting gear pivotally coupled to the waveguide;

at least one wire coupled to the pivoting gear and the articulating portion of the outer sheath to articulate the articulating portion with respect to the non articulating portion of the outer sheath; and drive gear engageable with the pivoting gear.

3. An ultrasonic surgical clamp apparatus comprising:

a housing;

an outer sheath joined to said housing, the outer sheath having at least one articulating portion;

an articulating knob mounted on the housing;

an ultrasonic waveguide positioned within the outer sheath and having an end-effector extending distally of the distal end of the outer sheath, the waveguide having at least one articulating portion and a non-articulating portion, the waveguide further adapted to receive a vibrational energy and to propagate the vibrational energy from the non-articulating portion to the articulating portion; and an articulation mechanism including a pivoting gear pivotally coupled to the waveguide and a drive gear movable in response to movement of the articulation knob to effect angular movement of the articulating portion of the outer sheath with respect to the housing.

4. The surgical clamp apparatus of claim 3, wherein said pivoting gear defines a plurality of circumferentially extending grooves for receiving teeth of the drive gear.

5. The surgical clamp apparatus of claim 3 further including a rotational knob mounted on the outer sheath for effecting rotation of the waveguide with respect to the housing.

6. An ultrasonic surgical instrument comprising:

a waveguide having a first articulating portion and a non-articulating portion;

the non-articulating portion of the waveguide having a first end and a second end, the first end adapted to receive a vibrational energy and to propagate the vibrational energy from the first end to the second end of the non-articulating portion;

the first articulating portion of the waveguide having a first end and a second end, the first end adapted to receive the vibration energy and to propagate the vibrational energy from the first end to the second end of the first articulating portion, the first end of the first articulating component being in contact with the second end of the non-articulating portion, the first articulating portion being movable to selected angles with respect to the non-articulating portion of the waveguide.

7. The surgical instrument of claim 6 further comprising a second articulating portion having a first end a second end, the first end adapted to receive the vibration energy and to propagate the vibration energy from the first end to the second end of the second articulating portion, the first end of the second articulating portion being in contact with the second end of the first articulating portion.

8. The surgical instrument of claim 6 wherein the first articulating portion is configured to be moved in and out of longitudinal alignment with the non-articulating portion.

9. The surgical instrument of claim 6 wherein the first end of the first articulating portion is pivotally coupled to the second end of the non-articulating portion.

10. The surgical instrument of claim 6 wherein the articulating portion of the waveguide configured for movement between a first position where the articulating portion is disposed at an angle to the non-articulating portion the waveguide and a second position where the articulating portion of the waveguide is substantially coaxial with the non-articulating portion of the waveguide.

11. The surgical instrument of claim 6 wherein the second end of the non-articulating portion includes one of a non-threaded cavity and a non-threaded projection.

12. The surgical instrument of claim 6 wherein the waveguide includes a controllably-articulated section.

13. The surgical instrument of claim 6 wherein the first end of the first articulating portion has one of a non-threaded projection and a non-threaded cavity.

14. The surgical instrument of claim 6 wherein the waveguide is rotatable with respect to a housing of the instrument.

15. The surgical instrument of claim 6 wherein the waveguide includes a plurality of articulating components.

16. The surgical instrument of claim 6 further comprising means for articulating the first articulating portion between a first position substantially parallel to the longitudinal axis of the non-articulating portion and a second position substantially angularly disposed with respect to the longitudinal axis of the non-articulating portion.

17. The surgical instrument of claim 6 further comprising an articulating mechanism associated with the surgical instrument to move the articulating portion of between a plurality of angular positions with respect to the non-articulating portion.

18. The surgical instrument of claim 17 wherein the articulating mechanism includes at least one reciprocating tension member configured to effect pivotal movement of the articulating portion.

19. The surgical instrument of claim 17 wherein the articulating mechanism comprises at least two tension members arranged on opposite sides of the articulating section.

20. The surgical instrument of claim 19 wherein the articulating mechanism includes a pivot gear to exert a force on one of the tension members while controllably releasing force on the opposite tension member.

21. A surgical apparatus comprising:

a first component having a first end a second end, the first end adapted to receive vibrational energy and to propagate the vibrational energy from the first end to the second end of the first component;

a second component having a first end a second end, the first end adapted to receive the vibrational energy and to propagate the vibration energy from the first end to the second end of the second component, the first end of the second component being in contact with the second end of the first component, the second component being movable in and out of longitudinal alignment with the first component.

22. The surgical instrument of claim 21 further comprising an articulating mechanism associated with the surgical apparatus, the articulating mechanism configured to control the articulation of the second component in at least one plane of articulation.

23. The surgical instrument of claim 21 further including a rotational mechanism associated with the surgical apparatus, the rotational mechanism configured to control the rotation of the second component about its axis of elongation.

24. An ultrasonic surgical apparatus comprising:

a waveguide having a first component and a second component, the waveguide further adapted to receive a vibrational energy and to propagate the vibrational energy from the first component to the second component, and the second component being configurable in a first position substantially coaxially with the first component, and the second component being configurable in a second position at a selected angle to the first component.

25. An ultrasonic surgical instrument comprising:

a first transmission component having a first end and a second end, the first end of the first transmission component being adapted to receive ultrasonic vibrations, the second end of the first transmission component having a non threaded mating region; and a second transmission component adapted to receive ultrasonic vibrations from the first transmission component and having a first end and a second end, the first end of the second transmission component having a non-threaded mating region configured to interface with the non-threaded region of the second end of the first transmission component.

26. The surgical instrument of claim 25 wherein the mating region of the second transmission component is held in operable arrangement with the mating region of the first transmission component by a sheath.

27. An ultrasonic surgical instrument comprising:

a handle portion;

an ultrasonic transmission member for transmitting vibrational energy and extending distally from the handle portion, the ultrasonic member having a distal portion; and articulating means to move the distal portion in and out of longitudinal alignment with the rest of the ultrasonic member, wherein the distal portion is adapted to receive the vibrational energy from the ultrasonic transmission member.

28. An ultrasonic surgical device comprising:

a waveguide having an end-effector, the waveguide being adapted to receive ultrasonic vibrations and to propagate the ultrasonic vibrations to the end-effector, the end effector being movable between a first position where the end effector is disposed at an angle to at least a portion of the waveguide and a second position where the end-effector is substantially coaxial with the waveguide.

* * * * *